United States Patent
Saitoh et al.

[11] Patent Number: 5,813,989
[45] Date of Patent: *Sep. 29, 1998

[54] DRIVING MENTAL CONDITION DETECTING APPARATUS

[75] Inventors: Satoshi Saitoh; Mitsuo Yasushi; Kazuhiro Akiyama; Masatoshi Yanagidaira, all of Kawagoe, Japan

[73] Assignee: Pioneer Electronic Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 559,273

[22] Filed: Nov. 15, 1995

[30] Foreign Application Priority Data

Nov. 16, 1994 [JP] Japan .................................. 6-282219

[51] Int. Cl.⁶ .............................. A61B 5/00; G08B 23/00
[52] U.S. Cl. .......................................... 600/484; 340/576
[58] Field of Search .................................... 128/671, 731, 128/733, 732, 898; 340/575, 576, 990, 995; 600/484, 544, 545, 546, 898

[56] References Cited

U.S. PATENT DOCUMENTS

| | | | |
|---|---|---|---|
| 4,673,913 | 6/1987 | Akita et al. | 340/575 X |
| 4,679,648 | 7/1987 | Johansen | 340/576 X |
| 5,266,070 | 11/1993 | Hagiwara et al. | 600/27 |
| 5,485,385 | 1/1996 | Mitsugi | 340/990 X |
| 5,488,353 | 1/1996 | Kawakami et al. | 340/575 X |
| 5,513,110 | 4/1996 | Fujita et al. | 340/990 X |

Primary Examiner—Jennifer Bahr
Assistant Examiner—Stephen Huang
Attorney, Agent, or Firm—Sughrue, Mion, Zinn, Macpeak & Seas, PLLC

[57] ABSTRACT

A driving mental condition detecting apparatus for detecting a deterioration state of driving mental conditions such as sleepiness, fatigue, and impatience occurring in a driver on the basis of physiological data detected from the driver and road travel data of a vehicle derived from a navigation system, thereby generating an alarm.

24 Claims, 18 Drawing Sheets

FIG.11

| | |
|---|---|
| A1 | DEPARTURE TIME Ts |
| A2 | INITIAL HEARTBEAT NUMBER HRs |
| A3 | PRESENT HEARTBEAT NUMBER HR |
| A4 | MWSA |
| A5 | RSA |
| A6 | PRESENT TIME |
| A7 | CONTINUOUS DRIVING TIME S |
| A8 | AZIMUTH DISTRIBUTION $1/\sigma_a$ |
| A9 | SPEED DISTRIBUTION $1/\sigma_u$ |
| AA | MOVEMENT DISTANCE L |
| AB | PRESENT RUNNING ROAD INFORMATION D |
| AC | SLEEPINESS OCCURANCE TIME T1 |
| AD | SLEEPINESS OCCURANCE TIME T2 |

| | |
|---|---|
| B1 | $S \cdot n1$ |
| B2 | $(1/\sigma_a + 1/\sigma_u) \cdot n2$ |
| B3 | 0 or n3 |
| B4 | $(RSA/MWSA) \cdot n4$ |
| B5 | $D \cdot n5$ |
| B6 | $Pn$ |
| B7 | $S \cdot h1$ |
| B8 | $(HRs - HR) \cdot h2$ |
| B9 | $(MWSA/RSA) \cdot h3$ |
| BA | $Ph$ |
| BB | $(S/L) \cdot e1$ |
| BC | $(MWSA/RSA) \cdot e2$ |
| BD | $Pe$ |

| | |
|---|---|
| C1 | RR1 |
| C2 | RR2 |
| C3 | RR3 |
| C4 | RR4 |

DRIVING MENTAL CONDITION DETECTING APPARATUS

BACKGROUND OF THE INVENTION

1. Field of the Invention

The invention relates to a driving mental condition detecting apparatus for detecting a driving mental condition of a driver during the driving of a vehicle.

2. Description of the Related Background Art

In recent years, there has been developed a driving mental condition detecting apparatus for detecting a deteriorated state of a driver during the driving of a vehicle, namely, sleepiness, fatigue, impatience, or the like and informing the driver of the detected condition, thereby urging safe driving.

In such a driving mental condition detecting apparatus, physiological data such as heartbeat, skin electric reaction and wink is obtained from the driver during the driving of the vehicle and mental conditions such as sleepiness, fatigue and impatience are judged on the basis of the physiological data.

In a situation during the driving of the vehicle, however, there is a problem such that an accurate judgment is not performed according to such a judging method of the mental conditions using only the physiological data.

SUMMARY OF THE INVENTION

The invention is made to solve the above problem and it is an object of the invention to provide a driving mental condition detecting apparatus which can accurately detect driving mental conditions of the driver during the driving of a vehicle.

A driving mental condition detecting apparatus according to the present invention comprises:

physiological data detecting means for detecting physiological data of a driver of a vehicle;

navigation means for obtaining travel data of the vehicle;

driving mental condition judging means for judging whether the driving mental conditions of the driver have deteriorated or not on the basis of the physiological data and the travel data;

and alarm generating means for generating an alarm when it is judged that the driving mental conditions deteriorated.

On the basis of the physiological data detected from the driver and the road travel data of the vehicle obtained from the navigation means, the deteriorated state of the driving mental conditions such as sleepiness, fatigue, and impatience occurring in the driver is detected, thereby generating an alarm.

BRIEF DESCRIPTION OF THE DRAWINGS

FIG. 11 is a diagram showing a memory map of an RAM;

DETAILED DESCRIPTION OF THE PREFERRED EMBODIMENTS

Figure 1:
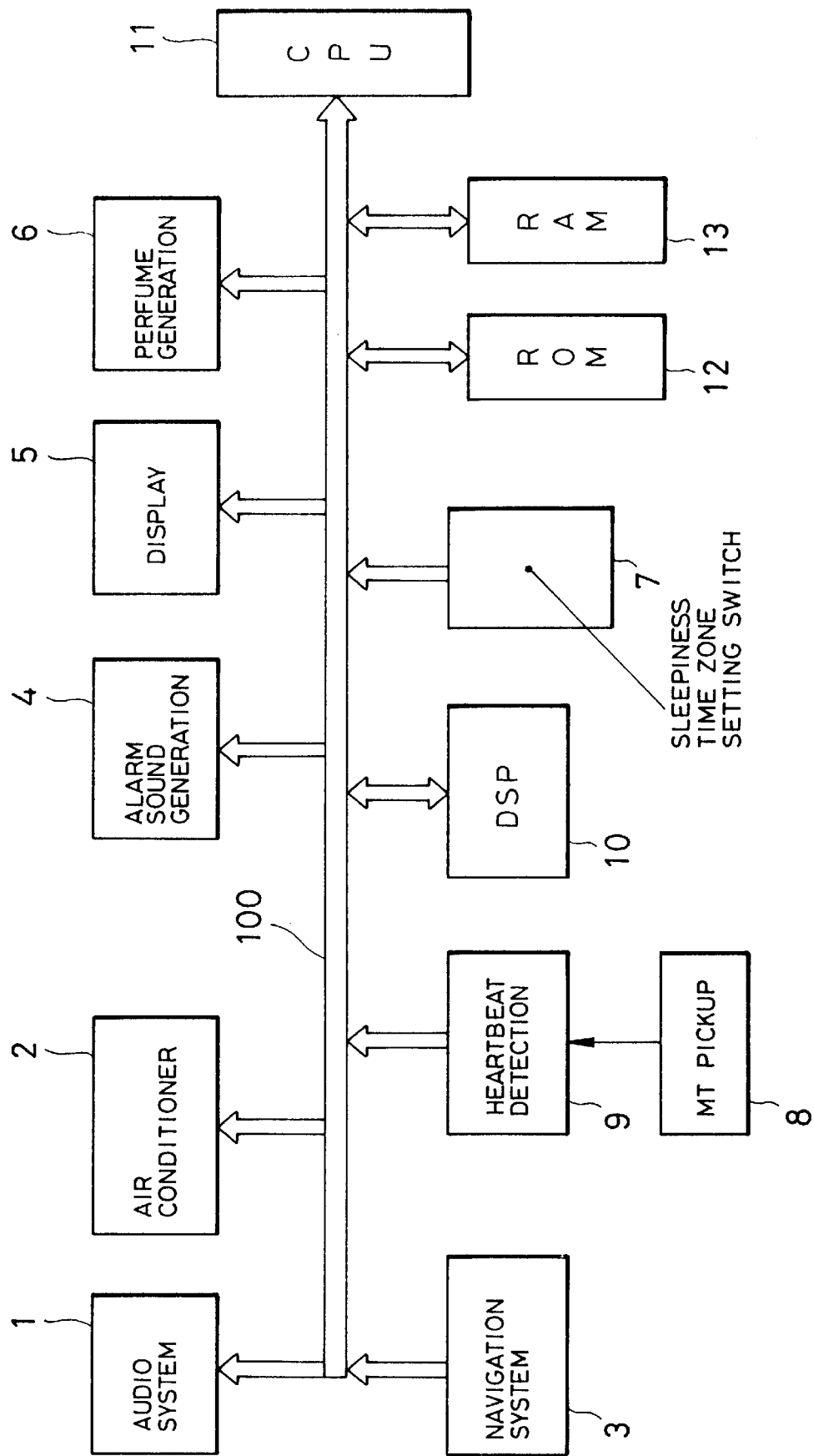
FIG. 1 is a diagram showing a construction of a car accessary system to which a driving mental condition detecting apparatus according to the invention is applied.

FIG. 1 is a diagram showing a construction of a car accessary system to which a driving mental condition detecting apparatus according to the invention is supplied.

In FIG. 1, an audio system 1 is what is called a car audio system comprising component elements such as a CD player, a tuner, a cassette deck, an equalizer, an amplifier, and speakers. The operations of the component elements in the audio system 1 are controlled in accordance with not only various kinds of operations by an operator but also various operation instruction signals which are supplied through a CPU bus 100 connected to a CPU 11.

An air conditioner 2 is a car air conditioner to adjust a temperature and a humidity in the room of the vehicle. The air conditioner 2 has a temperature sensor to detect the temperature in the room of the vehicle and automatically adjusts the temperature in the vehicle room to a predetermined set temperature on the basis of a detected temperature which is derived from the temperature sensor. Namely, a cool wind or a hot wind is blown into the room through blowing opening ports until the detected temperature is equal to a predetermined set temperature. The operation including the automatic temperature adjusting operation of the air conditioner system 2 is controlled in accordance with various operation instruction signals which are supplied through the CPU bus 100. The air conditioner system 2 transmits the detection temperature information obtained from the temperature sensor to the CPU bus 100.

A navigation system 3 is a car navigation system for navigating the vehicle to a predetermined target location by detecting the present location of the vehicle and displaying the detected present location on a display by linking with map information.

Figure 2:
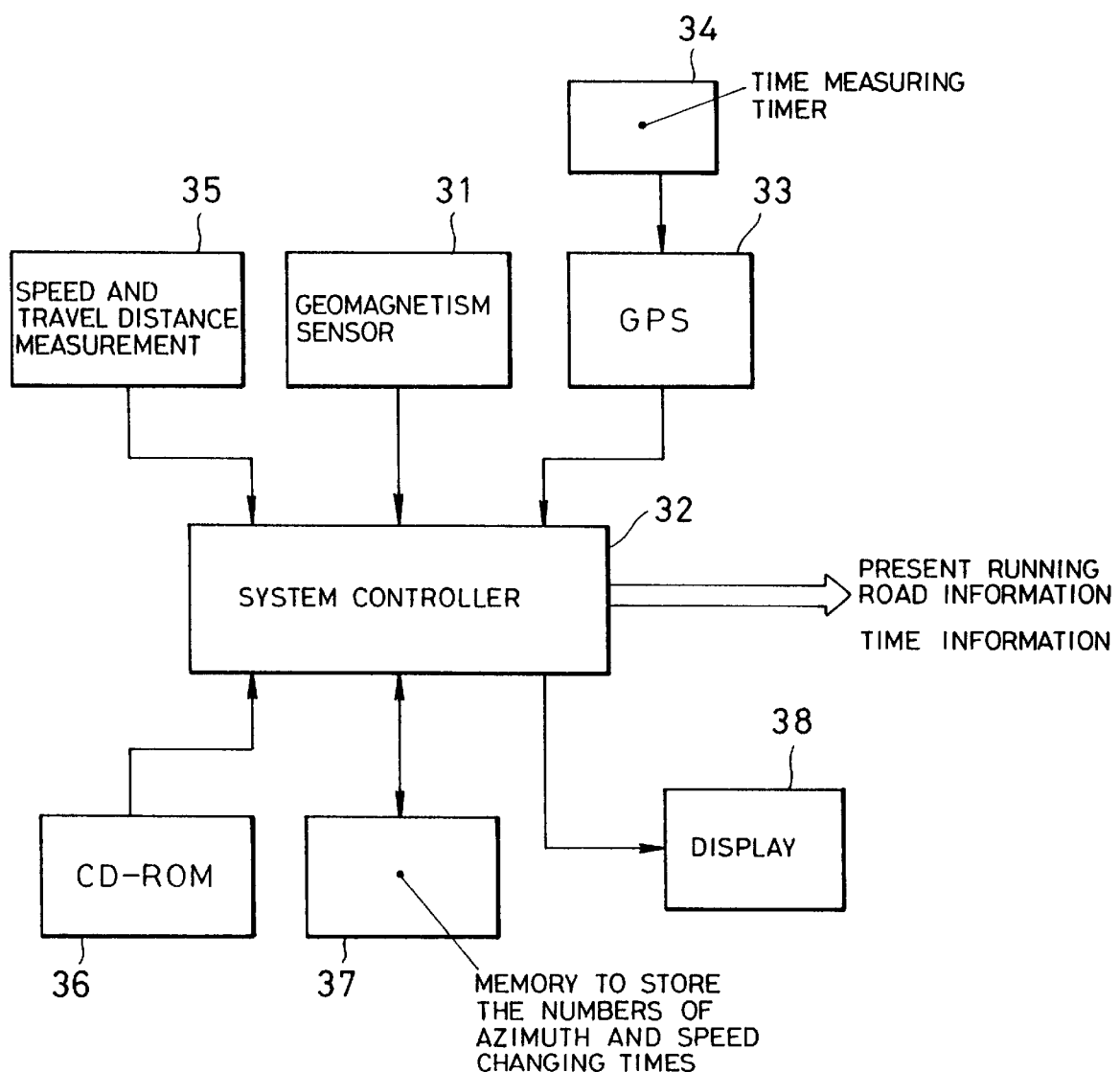
FIG. 2 is a diagram showing an example of a construction of a navigation system.

FIG. 2 is a diagram showing an example of a construction of the navigation system 3.

In FIG. 2, a geomagnetism sensor 31 detects a geomagnetism (magnetic field of the earth) state at the present location of the vehicle, generates azimuth information corresponding to a progressing azimuth of the vehicle on the basis of the detected geomagnetism state, and supplies it to a system controller 32. A GPS (Global Positioning System) 33 receives present time information that is supplied from a time measuring timer 34 and distance measurement signals which are transmitted from a plurality of GPS satellites, measures a latitude and a longitude at the present location of the vehicle, and supplies latitude and longitude information to the system controller 32. A speed and travel distance measuring apparatus 35 measures a running speed of the vehicle and an accumulated travel distance from the engine start point of the vehicle, and supplies the running speed and accumulated travel distance information to the system controller 32. In addition to the distance measurement signal as position information, time data is also included in the signal that is transmitted from the GPS satellite. Thus, by obtaining the present time from the time data, the time measuring timer 34 is unnecessary. If the accumulated travel distance from the engine start point of the vehicle is calculated from the start position and the present location and the speed of the vehicle is calculated as an average speed in a certain interval from the travel distance and the elapsed time of the interval, the speed and travel distance measuring apparatus 35 is unnecessary.

A CD-ROM player 36 reads recording information from a recording disk on which map information and various kinds of road information have been recorded, obtains reproduction map information and road information, and supplies them to the system controller 32.

The system controller 32 counts the number of azimuth changing times of the vehicle on the basis of the azimuth information supplied from the geomagnetism sensor 31 and stores it into an azimuth and speed changing times memory 37. The system controller 32 counts the number of changing times of the acceleration or deceleration of the vehicle on the basis of the running speed information supplied from the speed and travel distance measuring apparatus 35 and stores the count value into the memory 37. The system controller 32 further calculates the coordinates of the present location of the vehicle on a map on the basis of the azimuth, latitude and longitude information supplied from the geomagnetism sensor 31 and GPS 33 and supplies to a display 38 a video signal obtained by mixing a video signal such that an own vehicle location mark is displayed at the present location coordinate position and a video signal corresponding to the reproduction map information. On the basis of the present location coordinates and the reproduction map information, the system controller 32 judges a running road on which the vehicle is running at present. In the system controller 32, the road information corresponding to the running road decided as mentioned above is extracted from the road information supplied from the CD-ROM player 36 and transmitted as present running road information to the CPU bus 100. For example, identification information to distinguish a freeway and a general road can be mentioned as such road information. When it is judged that the road on which the vehicle is running at present is the freeway, the system controller 32 transmits the present running road information of a logic value "1" to the CPU bus 100. On the other hand, when it is judged that the present running road is the general road, the system controller 32 transmits the present running road information of a logic value "0" to the CPU bus 100.

In accordance with various read instruction signals supplied from the CPU bus 100, the system controller 32 reads out the information regarding the number of azimuth changing times of the vehicle and the number of speed changing times of the vehicle which have been stored in the memory 37 and transmits them to the CPU bus 100. Further, the system controller 32 transmits the present time information and the accumulated travel distance information to the CPU bus 100 in accordance with the various read instruction signals supplied from the CPU bus 100. The display 38 displays an image based on the video signal supplied.

An alarm sound generating apparatus 4 in FIG. 1 generates an alarm message, by a voice, corresponding to an alarm voice instruction signal that is supplied through the CPU bus 100. A display 5 displays the alarm message corresponding to an alarm display instruction signal that is supplied through the CPU bus 100. A perfume (smell) generating apparatus 6 generates a perfume with a stimulus into the room of the vehicle in accordance with a perfume generation instruction signal that is supplied through the CPU bus 100. A sleepiness time zone setting switch 7 generates a sleepiness time zone set request signal in accordance with a switching operation by a driver and transmits to the CPU bus 100. When the driver is conscious of a sleepiness by himself, he pushes the sleepiness time zone setting switch 7.

An MT (Minor Tremor) pickup 8 is attached on a seat belt equipped with the driver's seat. The MT pickup 8 detects a skin vibration level of approximately 1 to 10 microns occurring on the skin surface of the driver and supplies a skin vibration signal corresponding to the detected skin vibration level to a heartbeat detecting circuit 9.

Figure 3:
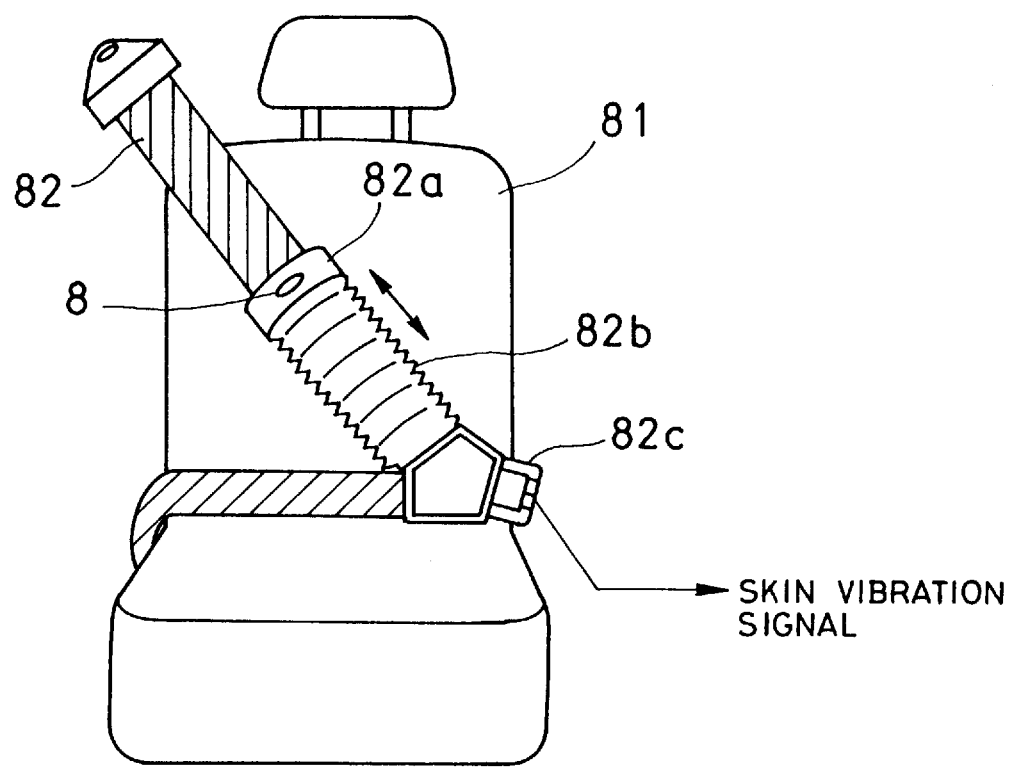
FIG. 3 is a diagram showing an example of an adhesion forming style of an MT pickup.

FIG. 3 is a diagram showing an example of an attaching style of the MT pickup 8.

In FIG. 3, a pickup fixing ring 82a is movably attached to a seat belt 82 equipped with a driver's seat 81. The MT pickup 8 is fixed on the pickup fixing ring 82a. A transmission cable for transmitting the skin vibration signal derived from the MT pickup 8 is connected to a seat belt buckle 82c through an expandable bellows member 82b surrounded the seat belt 82. Namely, the skin vibration signal generated from the MT pickup 8 is supplied to the heartbeat detecting circuit 9 through the seat belt buckle 82c.

When the seat belt 82 is fastened, the driver adjusts the pickup fixing ring 82a so that the skin vibration detecting surface of the MT pickup 8 is located at a position where it is come into contact with the driver. The MT pickup 8 doesn't need to directly touch the body of the driver. That is, it is sufficient that the skin vibration detecting surface of the MT pickup 8 is touched the driver through cloths and the seat belt 82.

The heartbeat detecting circuit 9 generates a heartbeat signal corresponding to the heartbeat of the driver on the basis of the supplied skin vibration signal and transmits the heartbeat signal to the CPU bus 100.

Figure 4:
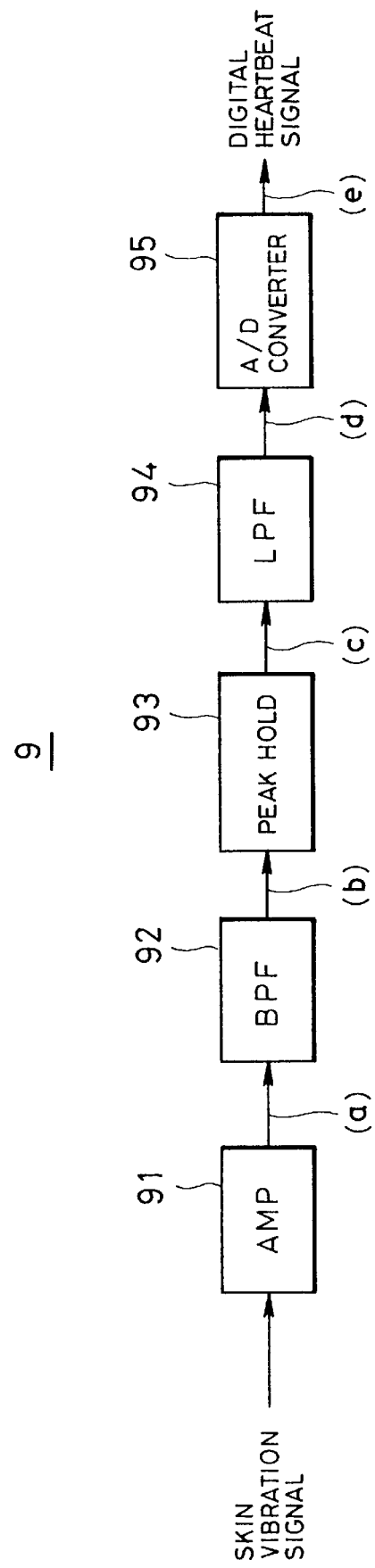
FIG. 4 is a diagram showing an internal construction of a heartbeat detecting circuit.

FIG. 4 is a diagram showing an internal construction of the heartbeat detecting circuit 9. FIGS. 5A to 5E are diagrams showing signal waveforms that are generated from respective component modules of the heartbeat detecting circuit 9.

In FIG. 4, an amplifier 91 amplifies a signal level of the skin vibration signal from which a high frequency noise component of the supplied skin vibration signal is eliminated, and supplies the amplified skin vibration signal (a) to a BPF (Band Pass Filter) 92. The BPF 92 is a band pass filter constructed so as to pass a component of 10 [Hz] of the amplified skin vibration signal (a). A passed skin vibration signal (b) is supplied to a peak holding circuit 93.

Figure 6:
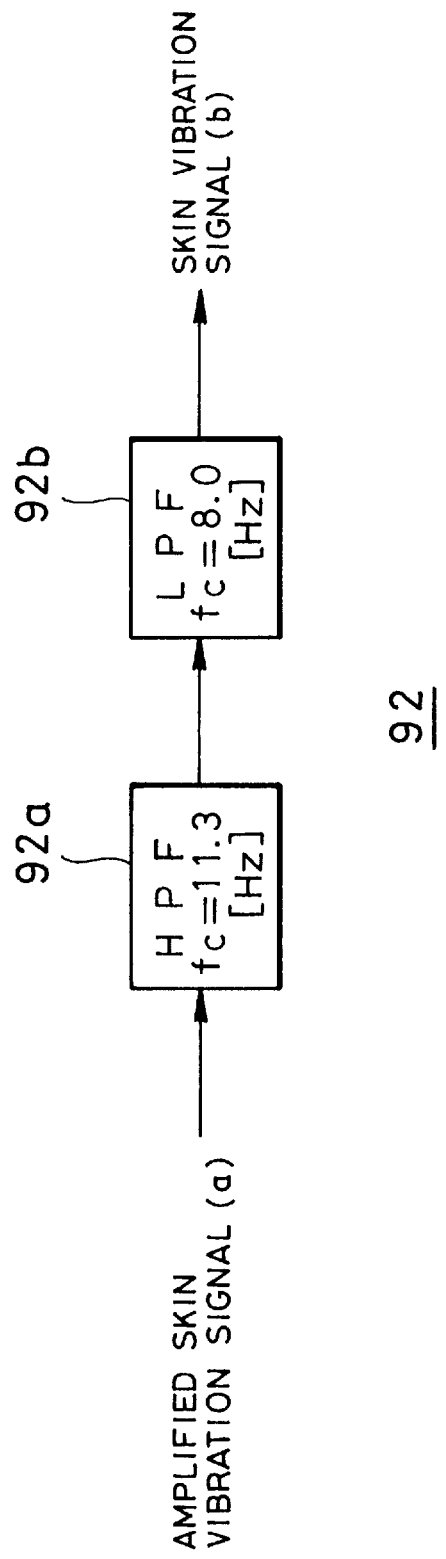
FIG. 6 is a diagram showing an example of an internal construction of a BPF.

FIG. 6 is a diagram showing an example of an internal construction of the BPF 92.

Figure 7:
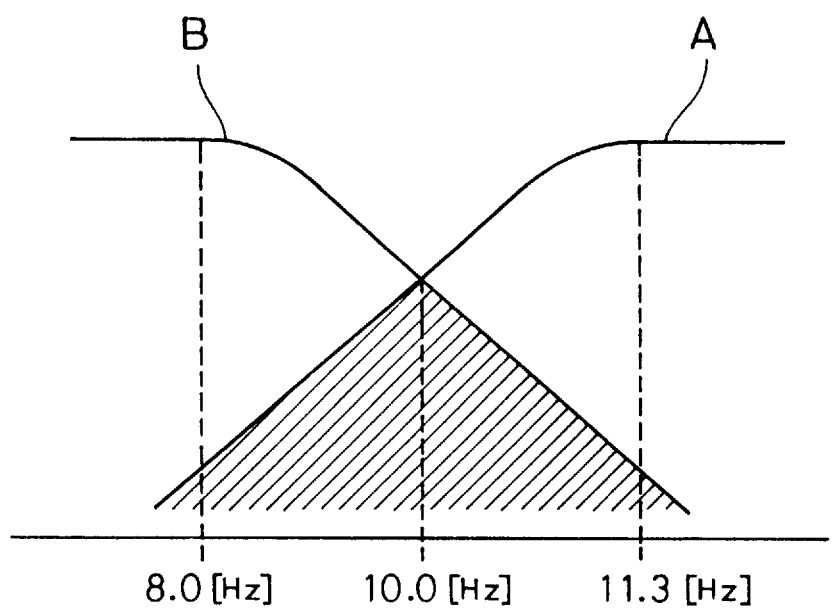
FIG. 7 is a diagram showing cut-off characteristics of an HPF and an LPF.

In FIG. 6, an HPF (High Pass Filter) 92a is a high pass filter having a cut-off frequency fc=11.3 [Hz] and its cut-off characteristics are shown by a solid line A in FIG. 7. An LPF (Low Pass Filter) 92b is a low pass filter having a cut-off frequency fc=8.0 [Hz] and its cut-off characteristics are shown by a solid line B in FIG. 7. According to the construction of the. BPF 92 as shown in FIG. 6, therefore, the skin vibration signal (b) comprising band components shown as a hatched portion in FIG. 7 is supplied to the peak holding circuit 93.

The peak holding circuit 93 generates a heartbeat signal (c) having an envelope waveform derived by holding each level peak value of the skin vibration signal (b). A time constant of the peak holding operation is set to, for example, 0.1 [second]. An LPF 94 obtains a heartbeat signal (d) from which noise components multiplexed to the heartbeat signal (c) are eliminated and supplies the heartbeat signal (d) to an A/D converter 95. For example, a cut-off frequency fc of the LPF 94 is set to fc=5.3 [Hz]. The A/D converter 95 samples the heartbeat signal d at a predetermined sampling timing, converts the sampled signal into a digital heartbeat signal (e) and transmits it to the CPU bus 100.

Namely, in the heartbeat detecting circuit 9, since the signal corresponding to the heartbeat has been multiplexed to a component of about 10 [Hz] in the skin vibration signal, the component of about 10 [Hz] is extracted from the skin vibration signal, and an envelope waveform signal derived by holding a level peak value of the extracted signal is set to a heartbeat signal corresponding to the heartbeat.

The reason why the cut-off frequency of the LPF 94 is so low to be 5.3 [Hz] as compared with that the desired signal includes a component of about 10 [Hz] in the skin vibration signal is because the LPF 94 is constructed by an analog circuit and such an analog filter has smooth cut-off characteristics, so that although the desired 10 [Hz] component slightly attenuates, a value such that an effect of a noise component elimination is larger than it is selected. That is, it is sufficient to set the cut-off frequency of the LPF 94 to a value such that the noise components can be effectively eliminated while sufficiently passing a desired frequency component.

Figure 8:
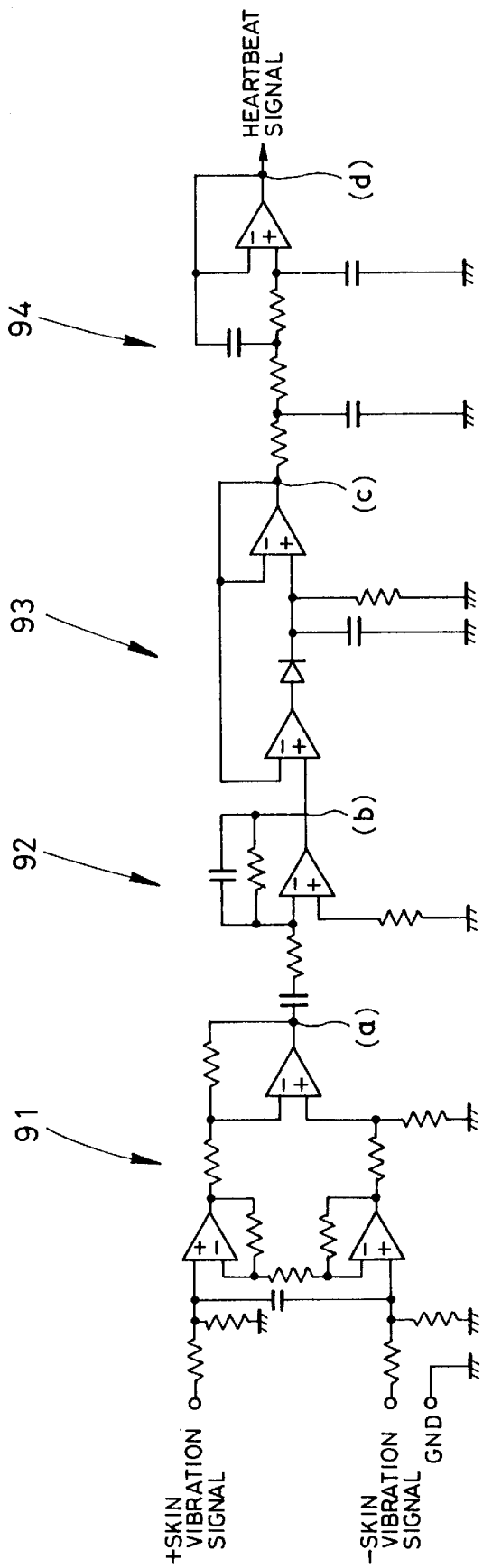
FIG. 8 is a diagram showing an example of a circuit construction of the heartbeat detecting circuit.

FIG. 8 is a diagram showing an example of a circuit construction to realize the heartbeat detecting circuit 9 as shown in FIG. 4.

As mentioned above, in a heartbeat measuring apparatus comprising the MT pickup 8 and heartbeat detecting circuit 9, the skin vibration of approximately 1 to 10 microns occurring on the skin surface of the driver is detected through the cloths of the driver and the seat belt 82 and the envelope waveform signal derived by holding the level peak value of the skin vibration signal corresponding to the skin vibration is derived as a heartbeat signal corresponding to the heartbeat.

According to such a heartbeat measuring apparatus, therefore, even when electrodes for detecting a heartbeat are not directly attached to a chest portion or a finger tip of the driver, the heartbeat can be measured.

A DSP (Digital Signal Processor) 10 in FIG. 1 executes an FFT (Fast Fourier Transformation) process to an RR signal supplied through the CPU bus 100 and measures a component of 0.05 to 0.15 [Hz] and a component of 0.15 to 0.4 [Hz] in the RR signal, respectively. The DSP 10 transmits the 0.05 to 0.15 [Hz] component in the RR signal as an MWSA (Mayer Wave related Sinus Arrhythmia) value and a 0.15 to 0.4 [Hz] component as an RSA (Respiratory Sinus Arrhythmia) value to the CPU bus 100.

Figure 5A:
FIGS. 5A to 5E is a diagram showing a signal waveform that is generated from each component module of the heartbeat detecting circuit.
Figure 5B:
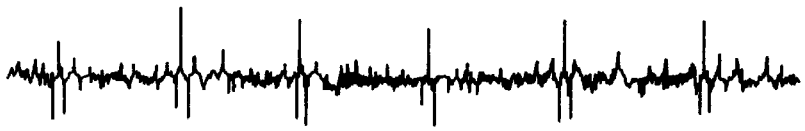
Figure 5C:
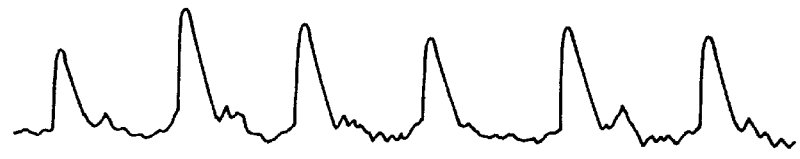
Figure 5D:
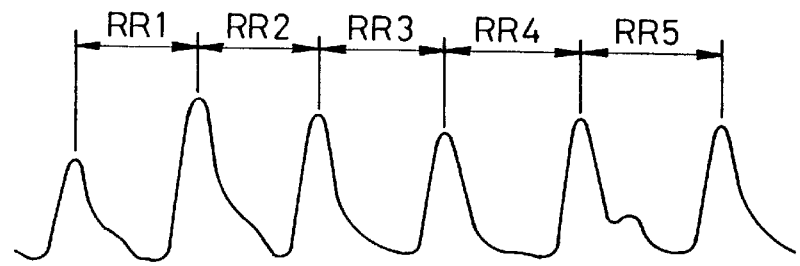

The RR signal is a signal obtained by time-serializing each heartbeat interval of the heartbeats. For example, the signal obtained by time-serializing each of heartbeat intervals RR1 to RR5 of the heartbeat signal (d) as shown in FIG. 5D is the RR signal. The MWSA value indicates a fluctuation of the heartbeat interval regarding a respiratory motion and it is known that the MWSA value is used as an activity index of the sympathetic system. The RSA value indicates a fluctuation of the heartbeat intervals regarding a blood pressure fluctuation and it is known that the RSA value is used as an activity index of the parasympathetic system.

A CPU (Central Processing Unit) 11 reads the foregoing various kinds of signals supplied to the CPU bus 100 in accordance with a driving mental condition detecting procedure stored in an ROM (Read Only Memory) 12 and transmits various kinds of instruction signals to the CPU bus 100. An RAM (Random Access Memory) 13 stores various information that is formed as intermediate data upon execution of the driving mental condition detecting procedure.

Figure 9:
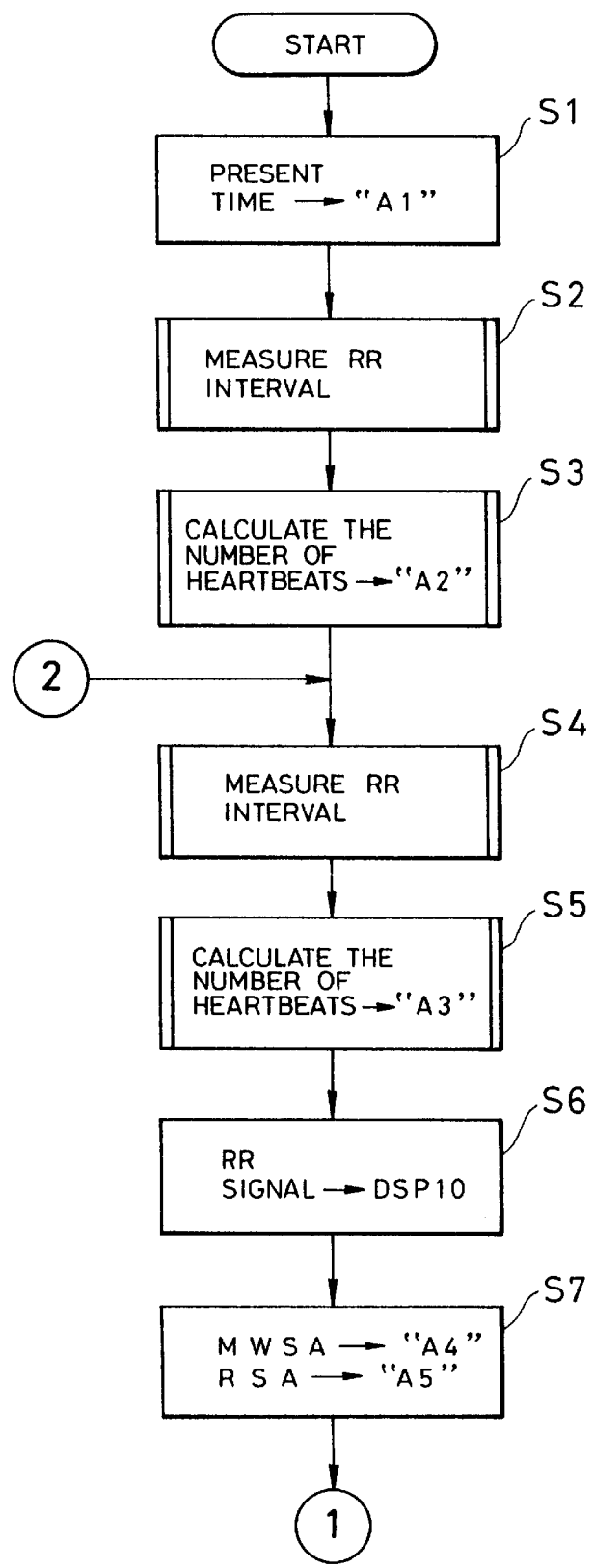
FIG. 9 is a flowchart showing a main flow of the driving mental condition detecting operation according to the invention.
Figure 10:
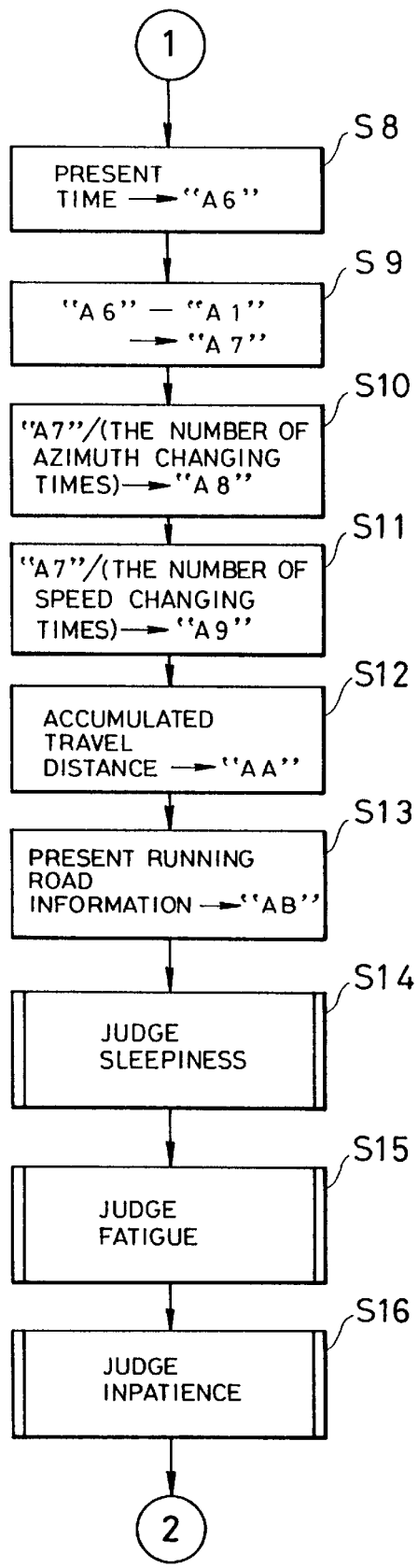
FIG. 10 is a flowchart showing a main flow of the driving mental condition detecting operation according to the invention.

FIGS. 9 and 10 are flowcharts showing a main flow for detection of the driving mental condition which is executed by the CPU 11 in response to an engine start of the vehicle. FIG. 11 is a diagram showing a memory map in the RAM 13 for storing various information that is formed as intermediate data upon execution of the main flow.

Figure 5E:
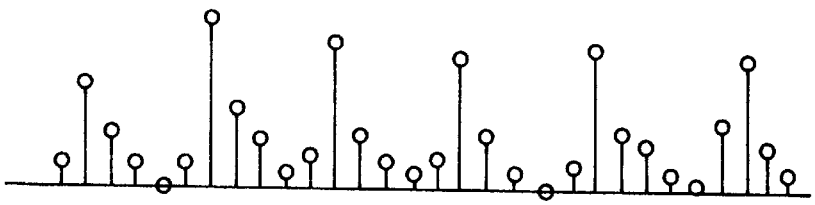

First, the CPU 11 reads the present time information from the navigation system 3 and stores the read present time information as departure time Ts into an address "A1" in the RAM 13 (step S1). Subsequently, the CPU 11 executes an RR measuring subroutine to measure a heartbeat interval RR of the heartbeat signal (step S2). In the RR measuring subroutine, the CPU 11 measures each heartbeat interval RR of the heartbeat signal for only a predetermined time on the basis of each sample value of the digital heartbeat signal (e), as shown in FIG. 5E, supplied from the heartbeat detecting circuit 9 and sequentially stores the measured heartbeat intervals RR into memory addresses after an address "C1" in the RAM 13. For example, the CPU 11 first sequentially detects a transition time point at which each sample value of the digital heartbeat signal (e) changes from an increasing tendency to a decreasing tendency. When each sample value of the digital heartbeat signal e doesn't change to the increasing tendency for an interval of 0.5 second from the transition detection time point, it is judged that the above transition detection time point is a signal peak timing. The CPU 11 subsequently sets a time interval of the adjacent signal peak timings judged to the heartbeat interval RR and sequentially stores them into the memory addresses after the address "C1" in the RAM 13.

After completion of the execution of the RR measuring subroutine, the CPU 11 starts to execute a heartbeat number calculating subroutine to obtain the number of heartbeats (step S3). In the heartbeat number calculating subroutine, the CPU 11 calculates the number of heartbeats per unit time on the basis of the heartbeat interval RR stored in each memory address after the "C1" address in the RAM 13 and stores the calculated number of heartbeats as an initial heartbeat number HRs into an address "A2" in the RAM 13. The total number of samples of the heartbeat intervals RR stored in the addresses after the "C1" address in the RAM 13 is divided by the total value of the heartbeat intervals obtained by adding the heartbeat intervals RR, so that the number of heartbeats per unit time can be obtained. After completion of the execution of the heartbeat number calculating subroutine, the CPU 11 starts to execute an RR measuring subroutine to measure the heartbeat interval RR of the heartbeat signal (step S4). Since the RR measuring subroutine are the same as the operation executed in step S2, its detailed description is omitted.

After completion of the execution of the RR measuring subroutine in step S4, the CPU 11 starts to execute the heartbeat number calculating subroutine to obtain the number of heartbeats (step S5). In the heartbeat number calculating subroutine, the CPU 11 calculates the number of heartbeats per unit time on the basis of the heartbeat interval RR stored in each memory address after the "C1" address in the RAM 13 and stores the calculated heartbeat number as a present heartbeat number HR into an address "A3" in the RAM 13. After completion of the execution of the heartbeat number calculating subroutine in step S5, the CPU 11 sequentially reads the heartbeat intervals RR stored in the memory addresses after the "C1" address in the RAM 13 and transfers them as an RR signal to the DSP 10 (step S6). By executing step S6, the DSP 10 executes the FFT process to the RR signal and transmits the 0.05 to 0.15 [Hz] component in the RR signal as an MWSA value and the 0.15 to 0.4 [Hz] component as an RSA value to the CPU bus 100. The CPU 11 fetches the MWSA value and RSA value, stores the MWSA value into an address "A4" in the RAM 13, and stores the RSA value into an address "A5" in the RAM 13 (step S7).

After that, the CPU 11 reads the present time information from the navigation system 3 and stores the read present time information as a present time T into an address "A6" in the RAM 13 (step S8). Subsequently, the CPU 11 reads each of the present time T stored in the address "A6" in the RAM 13 and the departure time Ts stored in the address "A1" in the RAM 13 and subtracts the departure time Ts from the present time T, thereby obtaining a continuous driving time S and storing into an address "A7" in the RAM 13 (step S9). The CPU 11 reads the information of the number of azimuth changing times of the vehicle from the navigation system 3, divides the number of azimuth changing times of the vehicle which was read, by the continuous driving time S stored in the address "A7" in the RAM 13, and stores the inverse number of the division result into an address "A8" in the RAM 13 as azimuth distribution parameter 1/σa (step S10). The CPU 11 reads the information of the number of speed changing times of the vehicle from the navigation system 3, divides the read number of speed changing times of the vehicle by the continuous driving time S stored in the address "A7" in the RAM 13, and stores the inverse number of the obtained division result into an address "A9" in the RAM 13 as a speed distribution parameter 1/σu (step S11).

The CPU 11 reads the accumulated travel distance information from the navigation system 3 and stores the read accumulated travel distance as a movement distance L into an address "AA" in the RAM 13 (step S12). The CPU 11 reads the present running road information from the navigation system 3 and stores the read present running road information as present running road information D into an address "AB" in the RAM 13 (step S13). After completion of step S13, the CPU 11 executes a sleepiness judging subroutine (step S14).

Figure 12:
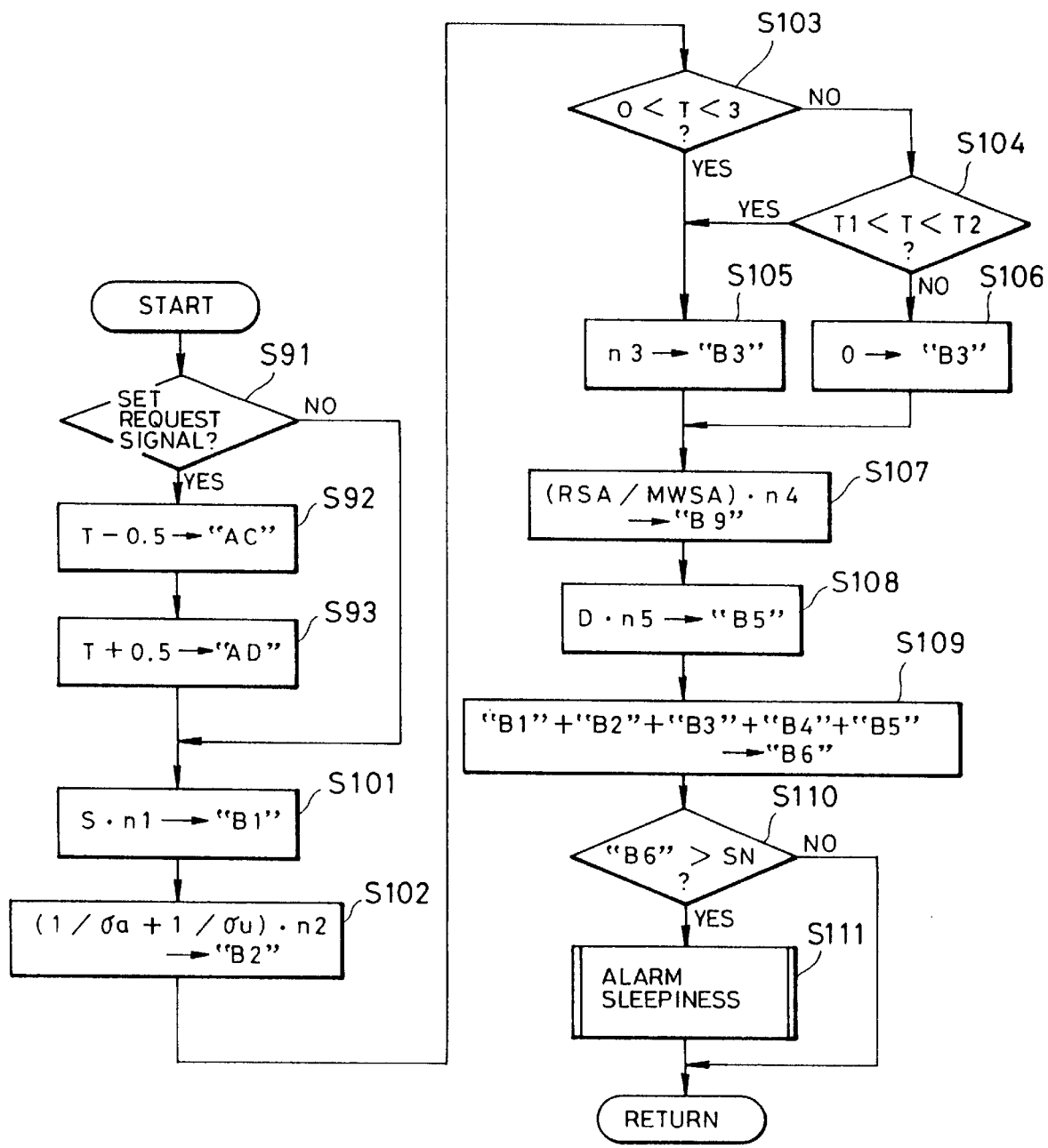
FIG. 12 is a flowchart showing a subroutine flow for a judgment of a sleepiness.

FIG. 12 is a flowchart showing a sleepiness judging subroutine.

In FIG. 12, the CPU 11 first judges whether a sleepiness time zone set request signal has been transmitted from the sleepiness time zone setting switch 7 or not (step S91). In step S91, when it is judged that the sleepiness time zone set request signal has been transmitted, the CPU 11 reads the present time T stored in the address "A6" in the RAM 13 and stores the time information obtained by subtracting 0.5 hour from the present time T into an address "AC" in the RAM 13 as a sleepiness occurrence time T1 (step S92). The CPU 11 stores the time information obtained by adding 0.5 hour to the present time T into address "AD" in the RAM 13 as a sleepiness occurrence time T2 (step S93). After completion of step S93 or if it is judged in step S91 that the sleepiness time zone set request signal is not transmitted, the CPU 11 reads the continuous driving time S stored in the address "A1" in the RAM 13 and stores S·n1 obtained by multiplying a sleepiness judgment coefficient n1 to the continuous driving time S into an address "B1" in the RAM 13 as a sleepiness judgment parameter based on the driving elapsed time (step S101).

The CPU 11 reads each of the azimuth distribution parameter 1/σa stored in the address "A8" in the RAM 13 and the speed distribution parameter 1/σu stored in the address "A9" in the RAM 13 and stores (1/σa+1/σu)·n2 obtained by multiplying a sleepiness judgment coefficient n2 to the addition result obtained by adding those parameters into an address "B2" in the RAM 13 as a sleepiness judgment parameter based on a monotonousness of the driving (step S102). The CPU 11 reads the present time T stored in the address "A6" in the RAM 13 and discriminates whether the present time T is a time within a range from 12 a.m. to 5 a.m. or a range from 1 p.m. to 3 p.m. or not (step S103). In step S103, if it is judged that the present time T is not the time within a range from 12 a.m. to 5 a.m. or a range from 1 p.m. to 3 p.m., the CPU 11 reads the sleepiness occurrence times T1 and T2 stored in the addresses "AC" and "AD" in the RAM 13 and judges whether the present time T is a time within a range from the sleepiness occurrence time T1 to T2 or not (step S104).

When it is judged in step S103 that the present time T is a time within a range from 12 a.m. to 5 a.m. or a range from 1 p.m. to 3 p.m. or when it is judged in step S104 that the present time T is a time within a range from the sleepiness occurrence time T1 to T2, the CPU 11 stores a sleepiness judgment coefficient n3 into address "B3" in the RAM 13 as a sleepiness judgment parameter based on the driving time zone (step S105). When it is judged in step S104 that the present time T is not a time within a range from the sleepiness occurrence time T1 to T2, the CPU 11 stores 0 into an address "B3" in the RAM 13 (step S106). After completion of step S105 or S106, the CPU 11 reads each of the MWSA value stored in the address "A4" in the RAM 13 and the RSA value stored in the address "A5" in the RAM 13 and stores (RSA/MWSA)·n4 obtained by multiplying a sleepiness judgment coefficient n4 to the division result obtained by dividing the RSA value by the MWSA value, into an address "B4" in the RAM 13 as a sleepiness judgment parameter based on an autonomic nervous system (step S107).

The CPU 11 reads the present running road information D stored in the address "AB" in the RAM 13 and stores D·n5 obtained by multiplying a sleepiness judgment coefficient n5 to the present running road information D into an address "B5" in the RAM 13 as a sleepiness judgment parameter based on the running road situation (step S108). The CPU 11 stores a sleepiness judgment value Pn obtained by adding the sleepiness judgment parameters stored in the addresses "B1" to "B5" in the RAM 13 as mentioned above into an address "B6" in the RAM 13 (step S109). Namely, by the execution of step S109, Sleepiness judgment value $Pn=S \cdot n1+(1/\sigma a+1/\sigma u) \cdot n2+n3+(RSA/MWSA) \cdot n4+D \cdot n5$ (1)

or

Sleepiness judgment value $Pn=S \cdot n1+(1/\sigma a+1/\sigma u) \cdot n2+(RSA/MWSA) \cdot n4+D \cdot n5$ (2)

is stored into an address "B6" in the RAM 13.

The CPU 11 judges whether the sleepiness judgment value Pn stored in the address "B6" in the RAM 13 is larger than a sleepiness judgment threshold value SN or not (step S110). When it is judged in step S110 that the sleepiness judgment value Pn is larger than the sleepiness judgment threshold value SN, the CPU 11 starts to execute a next sleepiness alarm subroutine (step S111).

In the sleepiness alarm subroutine, the CPU 11 supplies a play start instruction signal to a CD player in the audio system 1 and also supplies a high speed play instruction signal to raise a playing speed of the CD player. Further, the CPU 11 supplies a volume increase instruction signal to raise a sound volume of an amplifier in the audio system 1. The CPU 11 also supplies high and low frequency sounds increase instruction signal in order to increase high and low frequency sound components, to an equalizer in the audio system 1. By the above series of operations, the music piece in which the sound volume is large and the high and low frequency sounds are emphasized is generated as a sound at a playing speed higher than the ordinary speed.

In the above sleepiness alarm subroutine, the CPU 11 supplies a room temperature decrease instruction signal to the air conditioner system 2. In accordance with the room temperature decrease instruction signal, the air conditioner system 2 blows out a cool wind in order to reduce the temperature in the room by only a predetermined temperature than the present room temperature. The air conditioner system 2 adjusts the direction of the blowing ports so that the cool wind is directly blown to the driver. In the sleepiness alarm subroutine, the CPU 11 supplies a sleepiness alarm instruction signal to each of the alarm sound generating apparatus 4 and display 5. In response to the sleepiness alarm instruction signal, the alarm sound generating apparatus 4 generates a message, by a voice, to warn the driver of a fact that he is sleepy. On the other hand, in response to the sleepiness alarm instruction signal, the display 5 displays a message to warn the driver of a fact that he is sleepy. In the sleepiness alarm subroutine, the CPU 11 supplies a perfume generation instruction signal to the perfume generating apparatus 6. The perfume generating apparatus 6 generates a stimulus perfume into the vehicle room in response to the perfume generation instruction signal.

Namely, in the sleepiness judging subroutine shown in FIG. 12, the continuous driving elapsed time, monotonousness of the driving, driving time zone, and autonomic nervous state of the driver are used as parameters for judgment of the sleepiness and they are judged, thereby discriminating whether the driver feels sleepy or not.

For example, when the continuous driving time is long, or when the value of $S \cdot n1$ that is calculated in step S101 is large, a probability such that a sleepiness occurs is large. When the number of azimuth changing times of the vehicle per unit time and the number of accelerating times of the vehicle is reduced and the driving becomes monotonous, that is, when the value of $(1/\sigma a+1/\sigma u) \cdot n2$ that is calculated in step S102 is large, a probability such that the sleepiness occurs is large. When the driving time zone is a midnight, such a probability is large. In the above embodiment, when the driving time zone lies within a range from 12 a.m. to 5 a.m. or a range from 1 p.m. to 3 p.m., the sleepiness judgment coefficient n3 is added as a sleepiness judgment parameter. In the embodiment, even when the driving time zone is out of a range from 12 a.m. to 5 a.m. or a range from 1 p.m. to 3 p.m., so long as the driver himself is aware of the sleepiness and pushes the sleepiness time zone setting switch 7, the time zone of 0.5 hour before and after the time when the switch 7 was pushed is stored as a sleepiness time zone (steps S91 to S93). Finally, only when the vehicle is driven in the time zone within a range from 12 a.m. to 5 a.m. or a range from 1 p.m. to 3 p.m. and the sleepiness time zone sets as mentioned above, the sleepiness judgment coefficient n3 is added as a sleepiness judgment parameter (steps S103 to S106).

When the RSA value as an activity index of the parasympathetic system increases and the MWSA value as an activity index of the sympathetic system decreases, a possibility in which the sleepiness occurs in the driver is large. When the driver feels sleepy, therefore, the value of $(RSA/MWSA) \cdot n4$ that is calculated in step S107 is large.

During the driving of a freeway as compared with an ordinary road, a possibility such that a momentary sleepiness causes an accident is high. In the above embodiment, therefore, the information obtained by multiplying the sleepiness judgment coefficient n5 to the present running road information D indicating whether the road on which the vehicle is running at present is the freeway or not is added as a sleepiness judgment parameter. Since the present running road information D is set to a logic value "1" in case of the freeway as a present running road and is set to a logic value "0" in case of an ordinary road, eventually, only when the road on which the vehicle is at present running is the freeway, the sleepiness judgment coefficient n5 is added as a sleepiness judgement parameter. In the above embodiment, the sleepiness judgment parameter of the sleepiness judgment coefficient n5 is added in dependence on whether the road on which the vehicle is at present running is the ordinary road or the freeway. The invention, however, is not limited to such a construction. For example, it is also possible to construct in a manner such that information indicating whether the vehicle approaches a region where an accident frequently occurs or not is read out from the navigation system 3 as present running road information D and only when the present running road approaches the many-accident occurring region, a sleepiness judgment coefficient n6 is newly added as a sleepiness judgment parameter.

In the sleepiness judging subroutine, when the sleepiness judgment value Pn obtained by adding the above sleepiness judgment parameters is larger than the predetermined sleepiness judgment threshold value SN (steps S109 and S110), it is finally judged that the sleepiness occurs in the driver, so that a sleepiness warning is performed (step S111).

After completion of the sleepiness alarm subroutine in step S111 or when it is judged in step S110 that the sleepiness judgment value Pn stored in the address "B6" in the RAM 13 is not larger than the sleepiness judgment threshold value SN, the CPU 11 is returned to the execution of the main flow as shown in FIG. 10 and starts to execute a next fatigue judging subroutine (step S15).

Figure 13:
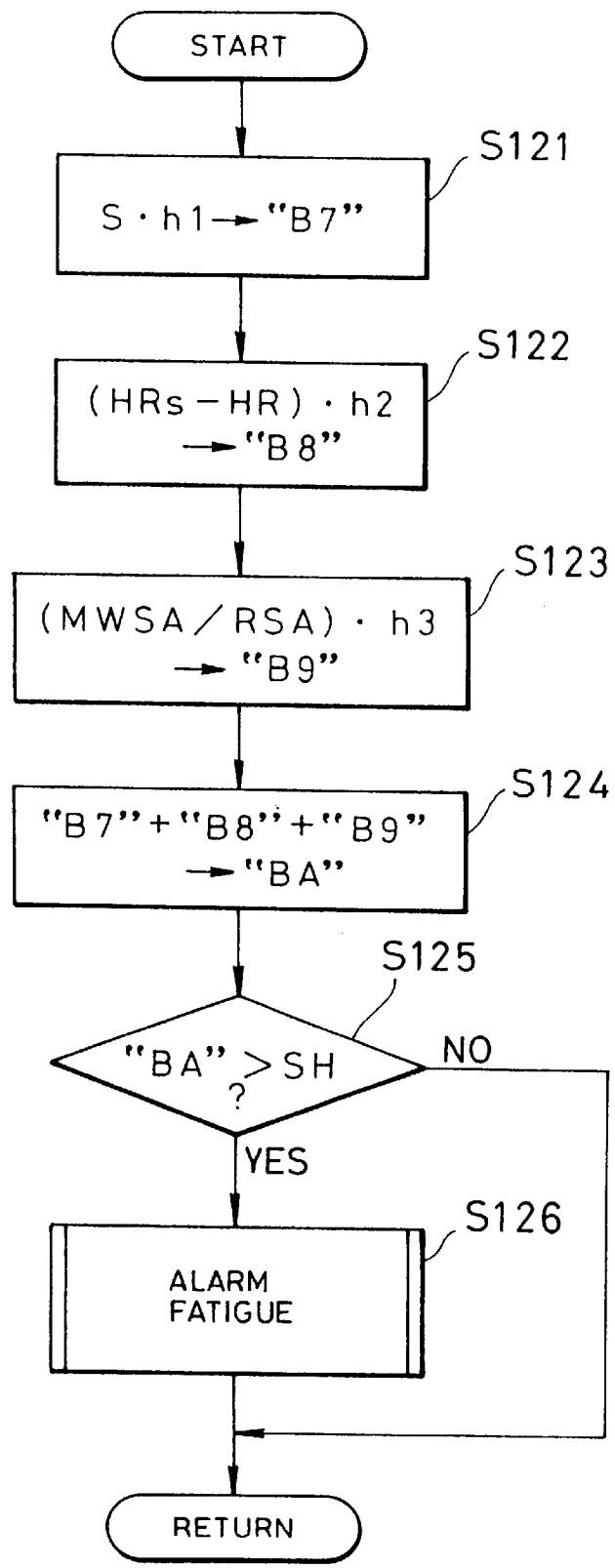
FIG. 13 is a flowchart showing a subroutine flow for a judgment of a fatigue.

FIG. 13 is a flowchart showing a flow for a fatigue judging subroutine.

In FIG. 13, the CPU 11 first reads the continuous driving time S stored in the address "A1" in the RAM 13 and stores $S \cdot h1$ obtained by multiplying a fatigue judgment coefficient h1 to the continuous driving time S into an address "B7" in the RAM 13 as a fatigue judgment parameter based on the driving elapsed time (step S121).

Subsequently, the CPU 11 reads each of the initial heartbeat number HRs stored in the address "A2" in the RAM 13 and the present heartbeat number HR stored in the address "A3" in the RAM 13 and stores (HRs−HR)·h2 obtained by multiplying a fatigue judgment coefficient h2 to the subtraction result obtained by subtracting them into an address "B8" in the RAM 13 as a fatigue judgment parameter based on the change in heartbeat number (step S122).

The CPU 11 reads each of the MWSA value stored in the address "A4" in the RAM 13 and the RSA value stored in the address "A5" in the RAM 13 and stores (MWSA/RSA)·h3 obtained by multiplying a fatigue judgment coefficient h3 to the division result obtained by dividing the MWSA value by the RSA value into an address "B9" in the RAM 13 as a fatigue judgment parameter based on the autonomic nervous system (step S123).

The CPU 111 stores a fatigue judgment value Ph obtained by adding the fatigue judgment parameters stored in the addresses "B7" to "B9" in the RAM 13 as mentioned above into an address "BA" in the RAM 13 (step S124). Namely, by executing step S124, $$\text{Fatigue judgment value } Ph = S \cdot h1 + (HRs - HR) \cdot h2 + (MWSA/RSA) \cdot h3 \qquad (3)$$

is stored in the address "BA" in the RAM 13.

Subsequently, the CPU 11 judges whether the fatigue judgment value Ph stored in the address "BA" in the RAM 13 is larger than a fatigue judgment threshold value SH or not (step S125). When it is judged in step S125 that the fatigue judgment value Ph is larger than the fatigue judgment threshold value SH, the CPU 11 starts to execute a fatigue alarm subroutine (step S126).

In the fatigue alarm subroutine, the CPU 11 supplies the play start instruction signal to the CD player in the audio system 1 and also supplies the high speed play instruction signal in order to raise the playing speed of the CD player. Further, the CPU 11 supplies the sound volume increase instruction signal in order to raise the sound volume of the amplifier in the audio system 1. The CPU 11 also supplies the high and low frequency sound increase instruction signal in order to increase the high and low frequency sound components, to the equalizer in the audio system 1. By the above series of operations, the music piece in which the sound volume is large and the high and low frequency sounds are emphasized is generated, by a sound, at the playing speed higher than the ordinary speed.

In the fatigue alarm subroutine, the CPU 11 supplies a fatigue alarm instruction signal to each of the alarm sound generating apparatus 4 and display 5. In response to the fatigue alarm instruction signal, the alarm sound generating apparatus 4 generates a message, by a voice, to make the driver active. For instance, the alarm sound generating apparatus 4 generates a message, by a voice, to advise a light exercise to the driver in response to the fatigue alarm instruction signal.

Namely, in the fatigue judging subroutine shown in FIG. 13, the continuous driving elapsed time, change in heartbeat number of the driver, and autonomic nervous state of the driver are used as parameters for the judgment of the fatigue and they are judged, thereby discriminating whether the driver feels a fatigue or not.

For example, when the continuous driving time is long, namely, when the value of S·h1 that is calculated in step S121 is large, a probability in which the driver is tired is high. When the number of heartbeats decreases, namely, when the value of (HRs−HR)·h2 that is calculated in step S122 is large, a possibility in which the driver is in a tired state is high. When the RSA value as an activity index of the parasympathetic system is small and the MWSA value as an activity index of the sympathetic system is large, namely, when the value of (MWSA/RSA)·h4 that is calculated in step S123 is large, a possibility such that the driver is tired is high.

In the fatigue judging subroutine, when the fatigue judgment value Ph obtained by adding the above fatigue judgment parameters is larger than the predetermined fatigue judgment threshold value SH (steps S124 and S125), it is finally judged that the driver is tired, so that a fatigue alarm is performed (step S126).

After completion of the fatigue alarm subroutine in step S126 or when it is judged in step S125 that the fatigue judgment value Ph stored in the address "BA" in the RAM 13 is not larger than the fatigue judgment threshold value SH, the CPU 11 is returned to the execution of the main flow as shown in FIG. 10 and starts to execute an impatience judging subroutine (step S16).

Figure 14:
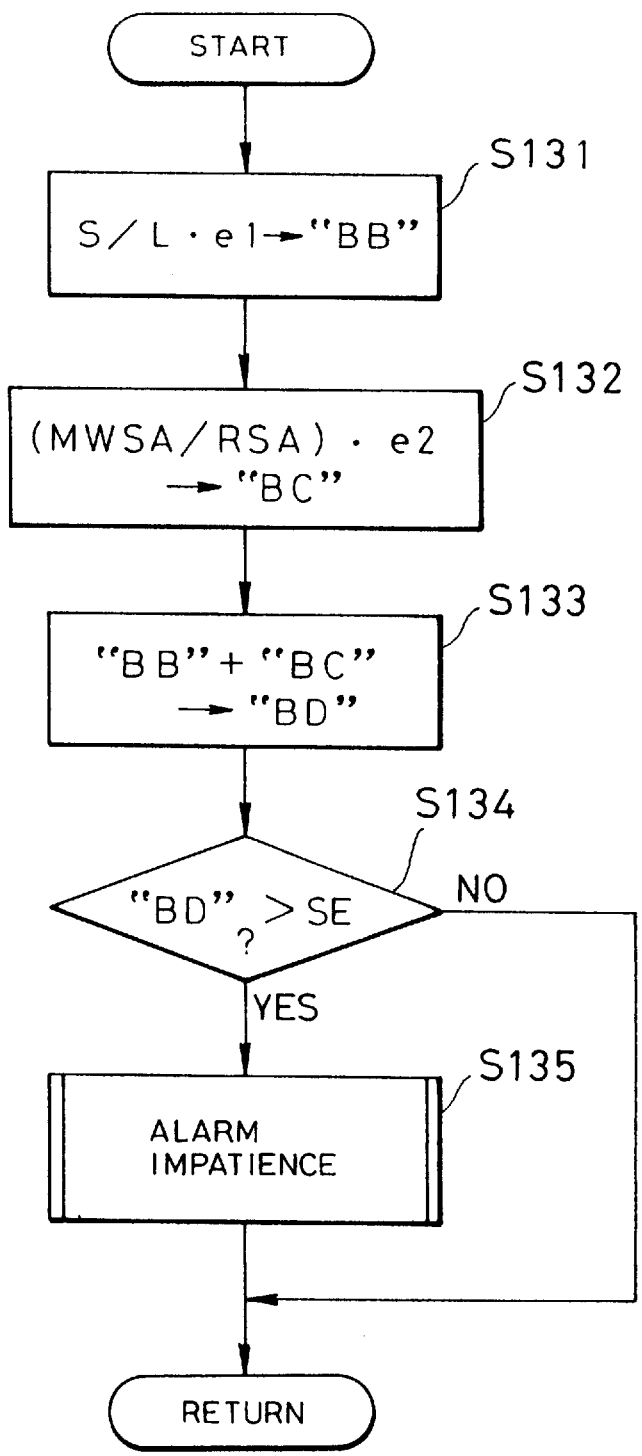
FIG. 14 is a flowchart showing a subroutine flow for a judgment of an impatience.

FIG. 14 is a flowchart showing a flow for the impatience judging subroutine.

In FIG. 14, the CPU 11 first reads the continuous driving time S stored in the address "A1" in the RAM 13 and the movement distance L stored in the address "AA" in the RAM 13 and divides the continuous driving time S by the movement distance L, thereby obtaining the inverse number of the movement distance per unit time. Further, (S/L)·e1 obtained by multiplying an impatience judgment coefficient e1 to the reciprocal number of the movement distance per unit time is stored in an address "BB" in the RAM 13 as an impatience judgment parameter based on the movement distance per unit time (step S131). The CPU 11 reads each of the MWSA value stored in the address "A4" in the RAM 13 and the RSA value stored in the address "A5" in the RAM 13 and stores (MWSA/RSA)·e2 obtained by multiplying an impatience judgment coefficient e2 to the division result obtained by dividing the MWSA value by the RSA value into an address "BC" in the RAM 13 as an impatience judgment parameter based on the autonomic nervous system (step S132).

The CPU 11 subsequently stores an impatience judgment value Pe obtained by adding the impatience judgment parameters stored in the addresses "BB" and "BC" in the RAM 13 into an address "BD" in the RAM 13 (step S133). Namely, by executing step S133, $$\text{Impatience judgment value } Pe = (S/L) \cdot e1 + (MWSA/RSA) \cdot e2 \qquad (4)$$

is stored in the address "BD" in the RAM 13.

The CPU 11 judges whether the impatience judgment value Pe stored in the address "BD" in the RAM 13 is larger than an impatience judgment threshold value SE or not (step S134). When it is judged in step S134 that the impatience judgment value Pe is larger than the impatience judgment threshold value SE, the CPU 11 starts to execute an impatience alarm subroutine (step S135).

In the impatience alarm subroutine, the CPU 11 supplies a low speed play instruction signal to the CD player in order to reduce the playing speed of the CD player in the audio system 1. Further, the CPU 11 supplies a sound volume decrease instruction signal in order to reduce the sound volume of the amplifier in the audio system 1. The CPU 11 supplies high and low frequency sound decrease instruction signal to reduce the high and low frequency sound components to the equalizer in the audio system 1. By the above series of operations, the sound volume of the music piece reproduced is reduced and, further, the playing speed is reduced than the ordinary speed.

In the impatience alarm subroutine, the CPU 11 supplies the impatience alarm instruction signal to each of the alarm sound generating apparatus 4 and display 5. In response to the impatience alarm instruction signal, the alarm sound generating apparatus 4 generates a message, by a voice, to soothe the nerves of the driver. For example, in response to the impatience alarm instruction signal, the alarm sound generating apparatus 4 generates a message, by a voice, to advise a deep breath to the driver. In the impatience alarm subroutine, the CPU 11 supplies a perfume generation instruction signal to the perfume generating apparatus 6. The perfume generating apparatus 6 generates a perfume such as to suppress the excited nerves into the vehicle room.

Namely, in the impatience judging subroutine shown in FIG. 14, the value of the inverse number of the movement distance of the vehicle per unit time and the autonomic nervous state of the driver are used as parameters for the judgment of the impatience and they are judged, thereby discriminating whether the driver is nervous or not.

For example, when the inverse number value of the movement distance of the vehicle per unit time, namely, the value of (S/L)·e1 that is calculated in step S131 is large, a probability such that a nervous feeling of the driver increases is high. When the RSA value as an activity index of the parasympathetic system is small and the MWSA value as an activity index of the sympathetic system is large, namely, when the value of (MWSA/RSA)·e2 that is calculated in step S132 is large, a possibility such that the driver is nervous is high.

In the impatience judging subroutine, when the impatience judgment value Pe obtained by adding those impatience judgment parameters is larger than the predetermined impatience judgment threshold value SE (steps S133 and S134), it is finally judged that the driver is nervous, so that an impatience alarm is performed (step S135).

After completion of the impatience alarm subroutine in step S135 or when it is judged in step S134 that the impatience judgment value Pe stored in the address "BD" in the RAM 13 is not larger than the impatience judgment threshold value SE, the CPU 11 is returned to the execution in step S4 of the main flow as shown in FIG. 9 and repetitively executes the operations as mentioned above.

As mentioned above, in the driving mental condition detection, first, by executing steps S4 to S7 of the main flow, various kinds of physiological data of the driver during the driving of the vehicle, namely, the heartbeat number HR, MWSA value, and RSA value are collected, respectively. By executing next steps S8 to S13, the real travel data of the vehicle, namely, the continuous driving time S, azimuth distribution parameter $1/\sigma a$, speed distribution parameter $1/\sigma u$, present running road information D, and movement distance L are respectively measured. By executing next steps S14 to S16, a deterioration state of the driving mental conditions of the driver, namely, sleepiness, fatigue, and impatience of the driver are detected. That is, when it is judged that the sleepiness occurs in the driver on the basis of the physiological data of the driver and the real travel data of the vehicle, the sleepiness alarm by the execution in step S111 is performed. When it is judged that a fatigue occurs in the driver on the basis of the physiological data and the real travel data of the vehicle, the fatigue alarm by the execution in step S126 is performed. When it is judged that the driver is nervous on the basis of the physiological data and the real travel data of the vehicle, the impatience alarm by the execution in step S135 is performed.

Figure 15:
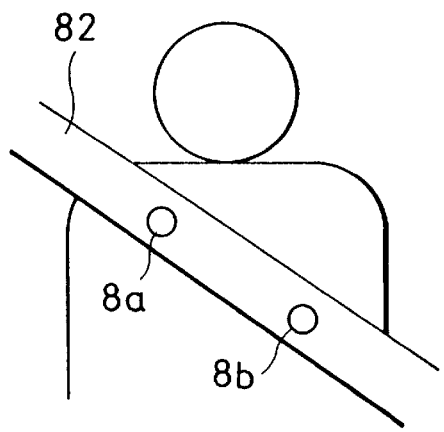
FIG. 15 is a diagram showing an example of another attachment style of the MT pickup.
Figure 16:
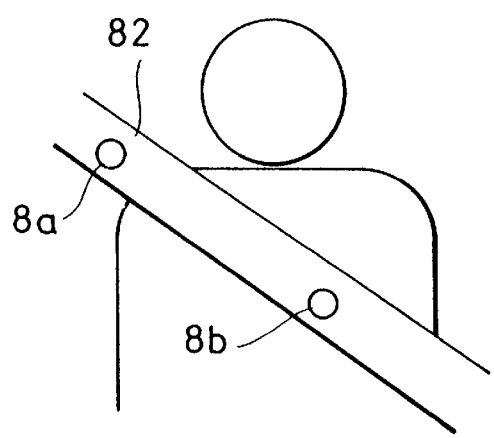
FIG. 16 is a diagram showing an example of still another attachment style of the MT pickup.
Figure 17:
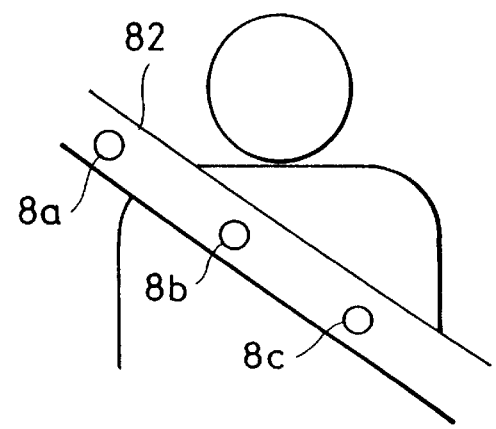
FIG. 17 is a diagram showing an example of further another attachment style of the MT pickup.

In the embodiment of FIG. 3, one MT pickup 8 has been attached to the seat belt 82. As shown in FIGS. 15 to 17, however, a plurality of MT pickups can be also provided at different positions on the seat belt 82.

FIG. 15 is a diagram showing an example in case of attaching two MT pickups 8a and 8b at two positions on the seat belt 82 to come into contact with the driver.

Figure 18:
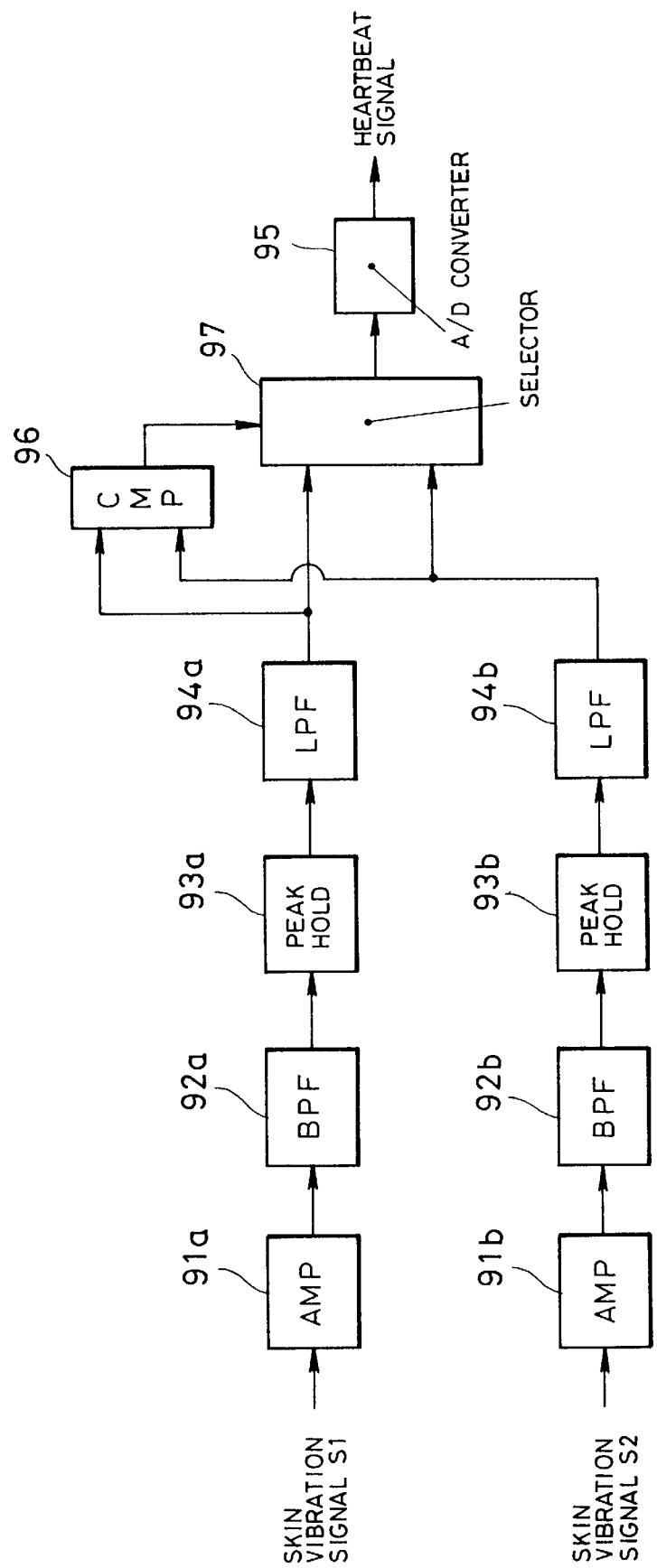
FIG. 18 is a diagram showing another embodiment of the heartbeat detecting circuit.

FIG. 18 is a diagram showing an example of a construction of the heartbeat detecting circuit 9 that is used when the MT pickups as shown in FIG. 15 are formed.

In FIG. 18, skin vibration signals S1 and S2 supplied from the MT pickups 8a and 8b are supplied to amplifiers 91a and 91b, respectively. The amplifier 91a, the BPF 92a, a peak holding circuit 93a, and an LPF 94a in FIG. 18 and, further, the amplifier 91b, the BPF 92b, a peak holding circuit 93b, and an LPF 94b have the same construction as that of the amplifier 91, BPF 92, peak holding circuit 93, and LPF 94 shown in FIG. 4. The skin vibration signal S1 supplied from the MT pickup 8a, therefore, is converted to the heartbeat signal by the construction comprising the amplifier 91a, BPF 92a, peak holding circuit 93a, and LPF 94a and is supplied to a comparator 96 and a selector 97. The skin vibration signal S2 supplied from the MT pickup 8b is converted to the heartbeat signal by the construction comprising the amplifier 91b, BPF 92b, peak holding circuit 93b, and LPF 94b and is supplied to the comparator 96 and selector 97. A construction comprising the comparator 96 and selector 97 selects the heartbeat signal at the high level from the heartbeat signals supplied from the LPFs 94a and 94b and supplies the selected heartbeat signal to the A/D converter 95.

Namely, according to the constructions as shown in FIGS. 15 and 18, the heartbeat signal is detected by using the skin vibration signal of a higher detecting sensitivity in the skin vibration signals which are generated from the two MT pickups 8a and 8b.

FIG. 16 is a diagram showing an example, in the two MT pickups 8a and 8b, when the MT pickup 8a is formed at the position where it is not come into contact with the driver and the MT pickup 8b is formed at the position on the seat belt 82 where the pickup 8b is come into contact with the driver.

Figure 19:
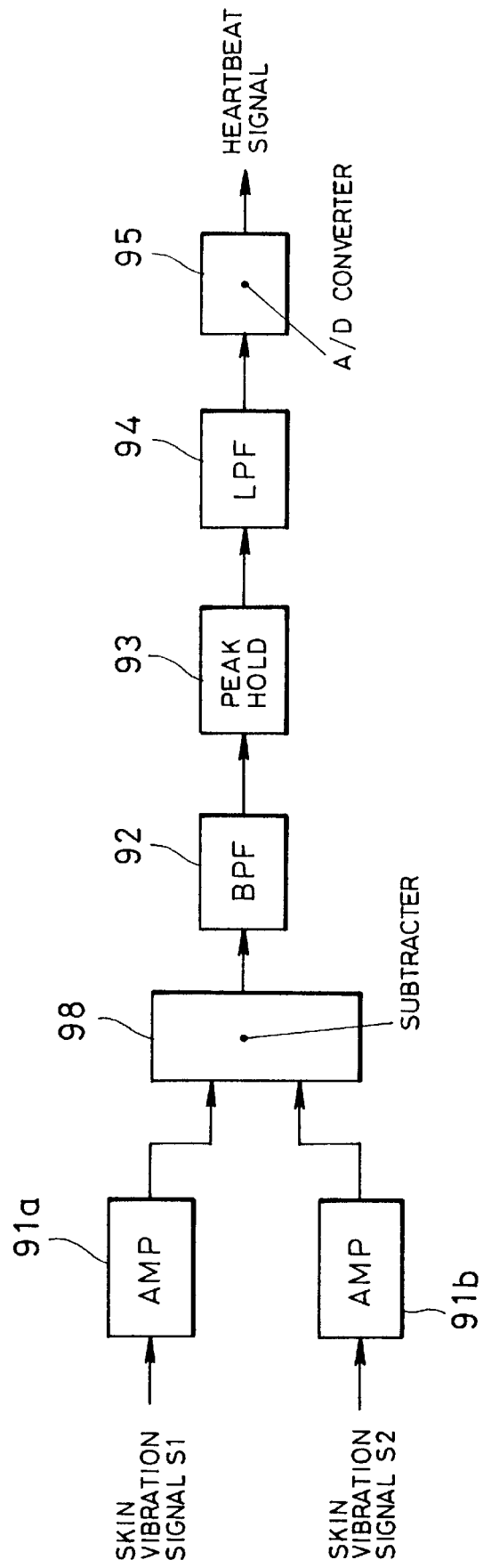
FIG. 19 is a diagram showing still another embodiment of the heartbeat detecting circuit.

FIG. 19 is a diagram showing an example of the construction of the heartbeat detecting circuit 9 using the MT pickups as shown in FIG. 16.

In FIG. 19, the skin vibration signals S1 and S2 supplied from the MT pickups 8a and 8b are supplied to a subtracter 98 through the amplifiers 91a and 91b. The subtracter 98 subtracts the levels of the supplied signals and supplies the resultant subtraction skin vibration signal to the BPF 92. The construction of the BPF 92, peak holding circuit 93, LPF 94, and A/D converter 95 has the same function as each functional module shown in FIG. 4.

Namely, according to the constructions as shown in FIGS. 16 and 19, a noise component of the same phase multiplexed to the skin vibration signal supplied from each of the MT pickup 8a provided at the position where it is not come into contact with the driver and the MT pickup 8b provided at the position where it is come into contact with the driver is reduced.

FIG. 17 is a diagram showing an example, among three MT pickups 8a, 8b, and 8c, when the MT pickup 8a is formed at a position where it is not come into contact with the driver and the MT pickups 8b and 8c are formed at positions on the seat belt 82 where they are come into contact with the driver.

Figure 20:
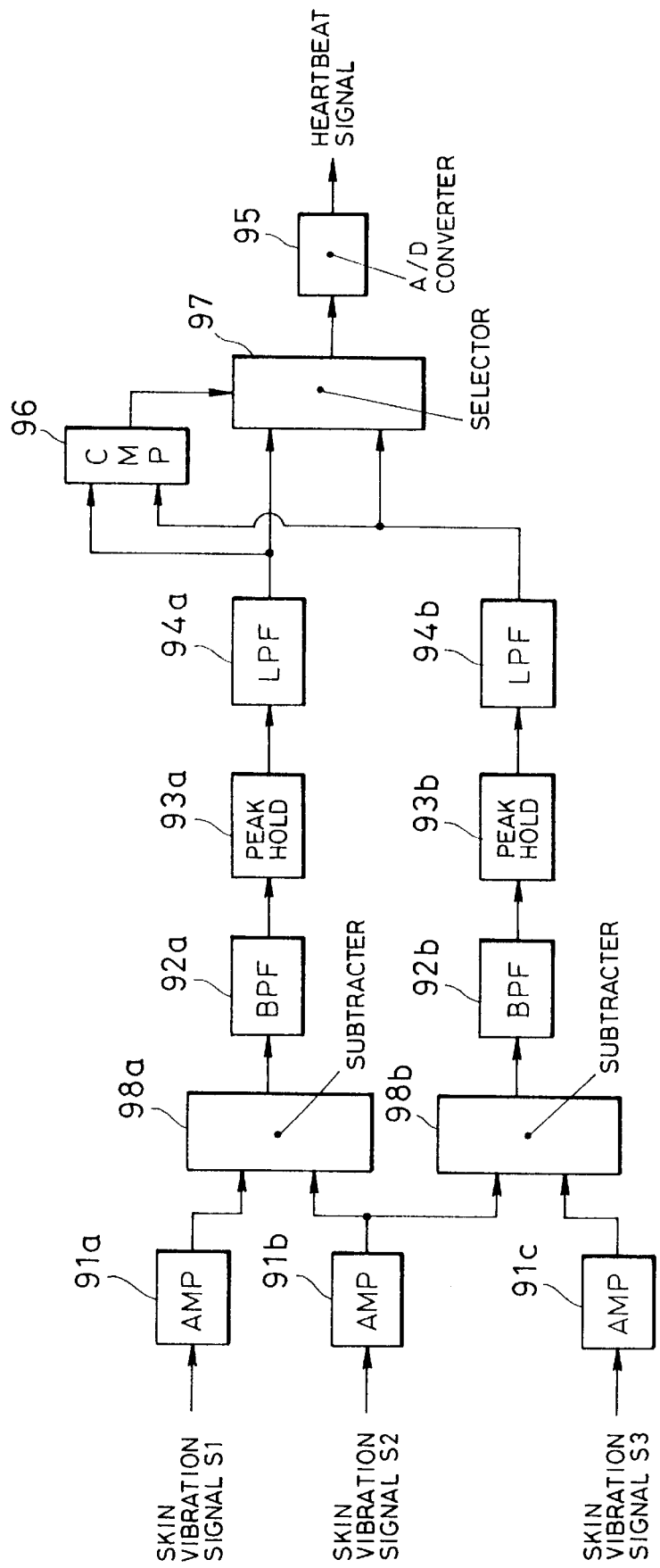
FIG. 20 is a diagram showing further another embodiment of the heartbeat detecting circuit.

FIG. 20 is a diagram showing an example of the construction of the heartbeat detecting circuit 9 using the MT pickups as shown in FIG. 17.

In FIG. 20, the skin vibration signals S1 and S2 supplied from the MT pickups 8a and 8b are supplied to a subtracter 98a through the amplifiers 91a and 91b. The subtracter 98a subtracts the levels of the supplied signals and supplies the resultant subtraction skin vibration signal to the BPF 92*a*. The construction of the BPF 92*a*, peak holding circuit 93*a*, and LPF 94*a* in FIG. 20 has substantially the same function as each functional module of the same reference numeral shown in FIG. 18.

On the other hand, skin vibration signals S2 and S3 supplied from the MT pickups 8*b* and 8*c* are supplied to a subtracter 98*b* through amplifiers 91*b* and 91*c*, respectively. The subtracter 98*b* subtracts the levels of those supplied signals and supplies the resultant subtraction skin vibration signal to the BPF 92*b*. The construction comprising the BPF 92*b*, peak holding circuit 93*b*, and LPF 94*b* in FIG. 20 has substantially the same function as that of each functional module of the same reference numeral shown in FIG. 18. The construction comprising the comparator 96 and selector 97 selects the heartbeat signal at the high level from the heartbeat signals supplied from the LPF 94*a* and 94*b* and supplies the selected heartbeat signal to the A/D converter 95.

Namely, according to the constructions as shown in FIGS. 17 and 20, the heartbeat signal detection is performed by using the skin vibration signal of a higher detecting sensitivity while reducing the noise component of the same phase multiplexed to the skin vibration signal.

In the driving mental condition detecting apparatus according to the invention as mentioned above, on the basis of the physiological data of the driver and the road travel data of the vehicle derived from the navigation system, a deterioration state of the driving mental conditions of the driver, namely, sleepiness, fatigue, and impatience are detected, thereby promoting to warn to the driver.

According to the driving mental condition detecting apparatus, therefore, even in a situation during the driving of the vehicle, a deterioration in driving mental conditions such as sleepiness, fatigue, and impatience of the driver can be accurately detected and when the deterioration in driving mental condition is detected, the detected result can be warned to at least the driver.

What is claimed is:

1. A driving mental condition detecting apparatus comprising:

physiological data detector for detecting physiological data of a driver of a vehicle;

navigator for obtaining travel data of said vehicle;

driving mental condition judger for judging a mental condition of a driver by multiplying each of said physiological data and said travel data by predetermined judgment coefficients, adding the products of the multiplications and comparing the sum of the products to a predetermined judgement threshold value; and alarm generator for generating an alarm when the sum of the products is greater than the predetermined judgement threshold value, thereby indicating that said driver has a deteriorated driving mental condition.

2. An apparatus according to claim 1, wherein said physiological data detector detects a number of heartbeats of said driver, an RSA (Respiratory Sinus Arrhythmia) value, and an MWSA (Mayer wave related Sinus Arrhythmia) value as said physiological data.

3. An apparatus according to claim 1, wherein said navigator obtains an accumulated travel distance of said vehicle, an azimuth change situation and a speed change situation of said vehicle, and present running road information corresponding to a road on which said vehicle is running as said travel data.

4. An apparatus according to claim 3, wherein said present running road information is information indicating whether said vehicle is running on an ordinary road or a freeway.

5. An apparatus according to claim 1, wherein said driving mental condition judger performs at least two of the following functions:

(a) multiplies a first sleepiness judgment coefficient by a continuous driving time to obtain a first sleepiness judgment value;

(b) multiplies a second judgment coefficient by a sum of an azimuth distribution parameter and a speed distribution parameter to obtain a second sleepiness judgment value representing monotonousness of driving;

(c) obtains a third sleepiness judgment value by using a third judgment coefficient based on a driving time zone;

(d) multiplies a fourth judgment coefficient by a quotient of an RSA (Respiratory Sinus Arrhythmia) value divided by an MWSA (Mayer wave related Sinus Arrhythmia) value to obtain a fourth sleepiness judgment value representing an autonomic nervous state of the driver; and (e) multiplies a fifth judgment coefficient by present running road information to obtain a fifth sleepiness judgment value representing a running road situation.

6. An apparatus according to claim 5, wherein said driving mental condition judging means adds at least two of said first through fifth judgment coefficients to obtain a total sleepiness judgment value, and determines whether said total sleepiness judgment value is larger than a predetermined sleepiness judgment threshold value.

7. An apparatus according to claim 1, wherein said driving mental condition is a state indicative of sleepiness.

8. An apparatus according to claim 7, wherein said driving mental condition judger multiplies a first sleepiness judgment coefficient by a continuous driving time to obtain a first sleepiness judgment value.

9. An apparatus according to claim 8, wherein said driving mental condition judger multiplies a second judgment coefficient by a sum of an azimuth distribution parameter and a speed distribution parameter to obtain a second sleepiness judgment value representing monotonousness of driving.

10. An apparatus according to claim 9, wherein said driving mental condition judging means obtains a third sleepiness judgment value by using a third judgment coefficient based on a driving time zone.

11. An apparatus according to claim 10, wherein said driving mental condition judger multiplies a fourth judgment coefficient by a quotient of an RSA (Respiratory Sinus Arrhythmia) value divided by an MWSA (Mayer wave related Sinus Arrhythmia) value to obtain a fourth sleepiness judgment value representing an autonomic nervous state of the driver.

12. An apparatus according to claim 11, wherein said driving mental condition judger multiplies a fifth judgment coefficient by present running road information to obtain a fifth sleepiness judgment value representing a running road situation.

13. An apparatus according to claim 1, wherein said driving mental condition is a state indicative of fatigue.

14. An apparatus according to claim 13, wherein said driving mental condition judger multiplies a continuous driving time by a first fatigue judgment coefficient to obtain a first fatigue judgment value.

15. An apparatus according to claim 14, wherein said driving mental condition judger subtracts a present heartbeat rate from an initial heartbeat rate and multiplies the result by a second fatigue judgment coefficient to obtain a second fatigue judgment value representing a change in heartbeat rate.

16. An apparatus according to claim 15, wherein said driving mental condition judger divides an MWSA (Mayer wave related Sinus Arrhythmia) value by an RSA (Respiratory Sinus Arrhythmia) value and multiplies the quotient by a third fatigue judgment coefficient to obtain a third fatigue judgment value representing an autonomic nervous state of the driver.

17. An apparatus according to claim 1, wherein said driving mental condition is a state indicative of impatience.

18. An apparatus according to claim 17, wherein said driving mental condition judger divides a continuous driving time by a movement distance and multiplies the quotient by a first impatience judgment coefficient to obtain a first impatience judgment value representing an inverse of movement distance per unit time.

19. An apparatus according to claim 18, wherein said driving mental condition judger divides an RSA (Respiratory Sinus Arrhythmia) value by an MWSA (Mayer wave related Sinus Arrhythmia) value and multiplies the quotient by a second impatience judgment coefficient to obtain a second impatience judgment value representing an autonomic nervous state of the driver.

20. A driving mental condition detecting apparatus comprising:

physiological data detecting means for detecting physiological data of a driver of a vehicle;

navigation means for obtaining travel data of said vehicle;

driving mental condition judging means for judging whether said driver feels sleepy based on said physiological data and said travel data; and alarm generating means for generating an alarm when it is judged that said driver feels sleepy, wherein said driving mental condition judging means judges sleepiness of said driver in accordance with said physiological data and said travel data during a predetermined driving period of time.

21. A driving mental condition detecting apparatus according to claim 20, wherein said predetermined driving period of time is a sleepiness time zone during which said driver may feel sleepy.

22. A driving mental condition detecting apparatus according to claim 20, wherein said predetermined driving period of time is from 12 a.m. to 5 a.m.

23. A driving mental condition detecting apparatus according to claim 20, wherein said predetermined driving period of time is from 1 p.m. to 3 p.m.

24. A driving mental condition detecting apparatus according to claim 20, wherein said predetermined driving period of time is from T−½ hour to T+½ hour, where T is a time selected by the driver.

* * * * *